(12) United States Patent
Pack et al.

(10) Patent No.: US 8,284,892 B2
(45) Date of Patent: Oct. 9, 2012

(54) SYSTEM AND METHOD FOR IMAGE RECONSTRUCTION

(75) Inventors: Jed Douglas Pack, Glenville, NY (US); Kai Zeng, Niskayuna, NY (US); Zhye Yin, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 960 days.

(21) Appl. No.: 12/340,787

(22) Filed: Dec. 22, 2008

(65) Prior Publication Data

US 2010/0158194 A1    Jun. 24, 2010

(51) Int. Cl.
*A61B 6/03* (2006.01)
(52) U.S. Cl. ............. 378/4; 378/210; 378/901; 382/131
(58) Field of Classification Search ............... 378/4, 210, 378/901; 382/131
See application file for complete search history.

(56) References Cited

U.S. PATENT DOCUMENTS

| 6,219,441 | B1 | 4/2001 | Hu |
| 7,424,088 | B2 | 9/2008 | Zamyatin et al. |
| 2005/0175144 | A1 | 8/2005 | Hsieh |
| 2006/0165271 | A1 | 7/2006 | Fischer et al. |
| 2006/0198491 | A1* | 9/2006 | Taguchi ........................... 378/15 |
| 2007/0253528 | A1* | 11/2007 | Ning et al. ....................... 378/15 |

FOREIGN PATENT DOCUMENTS

EP    1644897 A1    8/2007

OTHER PUBLICATIONS

Pack et al., A Novel Approach to Reconstruct Cone-Beam Data Acquired on Less than a Full Scan, Oct. 25, 2008, IEEE Nuclear Science Symposium, pp. 4229-4231.*

* cited by examiner

*Primary Examiner* — Toan Ton
*Assistant Examiner* — John Corbett
(74) *Attorney, Agent, or Firm* — Jason K. Klindtworth (57) ABSTRACT

A method of performing a computed tomographic image reconstruction is provided. The method provides for performing a short scan of an imaging object to acquire a short scan data, performing a plurality of image reconstructions based on the short scan data wherein the plurality of image reconstructions result in a corresponding plurality of image volumes wherein the image reconstructions use different view weighting functions, filtering the plurality of image volumes such that when the volumes are added together, the frequency domain data is substantially uniformly weighted. Further, the method provides for combining the plurality of image volumes together to produce a final image volume.

22 Claims, 10 Drawing Sheets

SYSTEM AND METHOD FOR IMAGE RECONSTRUCTION

BACKGROUND

Embodiments of the invention generally relate to imaging, and more particularly to a technique for reconstructing cone-beam data.

In a typical computed tomography (CT) system, an X-ray source projects a fan-shaped or cone-shaped beam, which is collimated to lie within an X-Y plane of a Cartesian coordinate system termed the "imaging plane." The X-ray beam passes through an object being imaged, such as a medical patient, and impinges upon an array of radiation detectors. The detector array includes detector elements, each of which measures the intensity of transmitted radiation along a beam projected from the X-ray source to the particular detector element. The intensity of the transmitted radiation is dependent upon the attenuation of the X-ray beam by the object and each detector produces a separate electrical signal that is a measurement of the beam attenuation. The signals are processed and reconstructed to form images which may be evaluated themselves or which may be associated to form a volume rendering or other representation of the imaged region. In a medical context, pathologies or other structures of interest may then be located or identified from the reconstructed or rendered volume.

During the past few years, significant progress has been made in the field of cone-beam tomography. Various exact and efficient techniques that allow accurate reconstruction for many different source trajectories such as helix, saddles, variable pitch helix, circle-plus-arc, and so forth, have been developed. Progress has also been made on developing algorithms for trajectories that do not satisfy Tuy's completeness condition everywhere in the imaging volume such as for the circular trajectory and for the circular segment trajectory. These trajectories satisfy Tuy's condition only at certain points within a single plane, yet data acquired along these paths is used to reconstruct volumetric data thereby resulting in cone-beam artifacts.

Cone-beam artifacts degrade the quality of the reconstructed CT images. Moreover, as CT scanners evolve to larger coverage, this problem becomes more critical. For example, cone-beam artifacts produce shading and glaring around high contrast edges in CT images. These artifacts are undesirable and may sometimes affect the quantitative robustness of CT numbers. Moreover, currently available traditional techniques fail to provide desired imaging quality due to cone-beam artifacts. Also, use of other currently available techniques result in new artifacts being introduced due to data truncation, additional interpolation and filtering. Further, traditional techniques of cone-beam reconstruction use weighting of different parts of the data by different amounts that result in high computational cost and time.

It is therefore desirable to provide an efficient and computationally less intensive reconstruction technique and to reduce cone-beam artifacts in CT images without compromising on image quality.

Brief Description

Briefly in accordance with one aspect of the technique a method of performing a computed tomographic image reconstruction is provided. The method provides for performing a short scan of an imaging object to acquire a short scan data, performing a plurality of image reconstructions based on the short scan data wherein the plurality of image reconstructions result in a corresponding plurality of image volumes wherein the image reconstructions use different view weighting functions, filtering the plurality of image volumes such that when the volumes are added together, the frequency domain data is substantially uniformly weighted. Further, the method provides for adding the plurality of image volumes together to produce a final image volume.

In accordance with another aspect of the present technique a tomographic imaging apparatus is provided. The apparatus includes a computer programmed to perform a short scan of an imaging object to acquire short scan data; The computer is further configured to perform a plurality of image reconstructions based on the short scan data wherein the plurality of image reconstructions result in a corresponding plurality of image volumes and wherein the image reconstructions use different view weighting function. Further, the computer is programmed to filter the plurality of image volumes such that when the volumes are added together, the frequency domain data is substantially uniformly weighted, the plurality of image volumes are combined together to produce a final image volume. The tomographic imaging apparatus includes a display unit for displaying the image. Computer programs that afford functionality of the type defined by this method may also be provided by the present technique.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
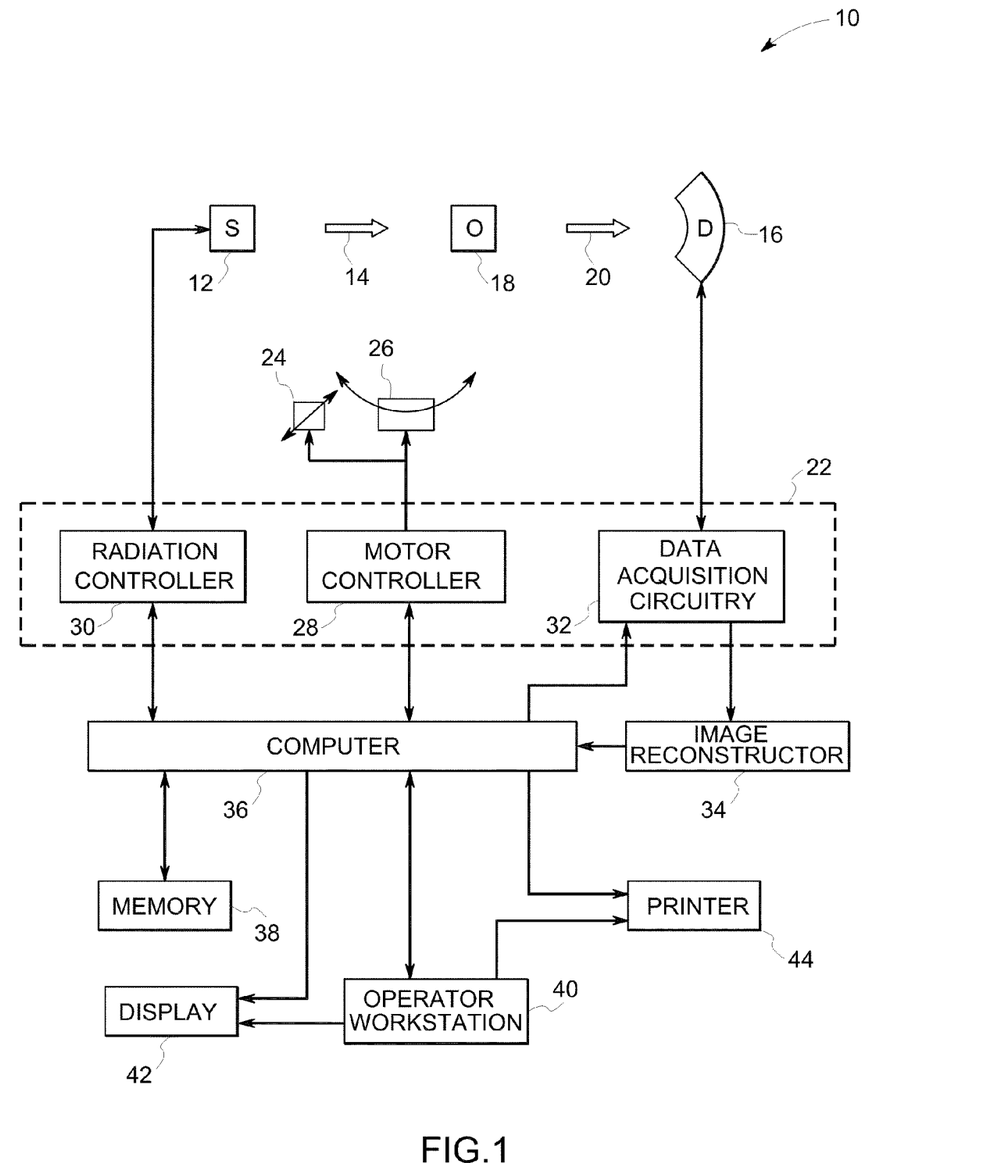
FIG. 1 is a block schematic diagram of a CT imaging system.

Embodiments of the present invention are generally directed to enhancing image quality and removing artifacts by an image reconstruction technique for cone-beam data. Referring now to FIG. 1, an imaging system 10 for use in accordance with the present technique is illustrated. The imaging system 10 is adapted to acquire projection images and to process the acquired projection images before reconstruction. In the illustrated embodiment, the imaging system 10 is shown as including a radiation source 12, such as an X-ray source. A collimator (not shown in FIG. 1) may be positioned adjacent to the radiation source 12 for regulating the size and the shape of a stream of radiation 14 that emerges from the radiation source 12.

In typical operation, the radiation source 12 projects a stream of radiation 14 towards an object 18 to be imaged and a detector array 16 placed on the side of the object 18 opposite the radiation source 12. The stream of radiation 14 passes into an imaging volume in which the object 18 to be imaged may be positioned. The object 18 may be a subject of interest such as a human patient, or, in other contexts, a part, package, or piece of luggage to be screened. It may be noted that a particular region of the object 18 may be chosen by an operator for imaging so that the most useful scan of the region may be acquired.

Further, reference numeral 20 may be representative of an attenuated portion of the radiation that passes through or around the object 18, which provides the attenuation, and impacts the detector array 16. It should be noted that portions of the radiation 14 may extend beyond the boundary of the object 18 and may also impact detector 16 without being attenuated by the object 18. The detector array 16 may be a single slice detector or a multi-slice detector and is generally formed as an array of detection elements. Each detector element, when impacted by the radiation 20, produces an electrical signal that represents the intensity of the attenuated radiation 20 incident at the position of the detector element. These signals are acquired and processed to reconstruct an image of the features internal as well external to the object 18.

The object 18 and the radiation source 12 may be displaced relative to each other, allowing projection data to be acquired at various views relative to the object 18 if desired. For example, the object 18 may be positioned on a table (not shown in FIG. 1), such as a turntable, so that the object 18 may be rotated during the examination process to expose all sides of the object 18 to the stream of radiation 14. Alternatively, the radiation source 12 and/or the detector array 16 may be disposed on a gantry (not shown in FIG. 1), which may be rotated around the object 18 during the examination process. As the object 18 and the radiation source 12 rotate relative to each other, the detector array 16 collects data of the attenuated radiation at various view angles relative to the object 18. Thus, an image or slice is acquired which may incorporate, in certain modes, less or more than 360 degrees of projection data, to formulate an image. It may be noted that in accordance with the present techniques a short scan which is typically a scan less than 360 degrees is used to formulate an image.

Operation of the radiation source 12 is controlled by a system controller 22, which furnishes both power, and control signals for examination sequences. Moreover, the detector array 16 may be operationally coupled to the system controller 22, which commands acquisition of the signals generated in the detector array 16. The system controller 22 may also execute various signal processing and filtration functions, such as for initial adjustment of dynamic ranges, interleaving of digital image data, and so forth. In general, system controller 22 commands operation of the imaging system 10 to execute examination protocols and to process acquired data. In the present context, system controller 22 may also include signal processing circuitry and other circuitry, typically based upon a general purpose or application-specific digital computer, associated memory circuitry for storing programs and routines executed by the computer, as well as configuration parameters and image data, interface circuits, and so forth. For example, the associated memory circuitry may store programs or codes for implementing the present technique. Moreover, the system controller 22 may be implemented as hardware and/or software components of the depicted computer 36.

In the embodiment illustrated in FIG. 1, the system controller 22 is shown as being operationally coupled to a linear positioning subsystem 24 and a rotational subsystem 26. In particular, the system controller 22 may include a motor controller 28 that controls the operation of the linear positioning subsystem 24 and the rotational subsystem 26. The rotational subsystem 26 enables the X-ray source assembly and/or the detector assembly to be rotated once or multiple times around the object 18. In one embodiment, the rotational subsystem 26 may include a gantry. As such, the system controller 22 may be utilized to control the rotational speed and position of the gantry. Alternatively, the rotational subsystem 26 may include a motorized turntable and the system controller 22 may be configured to rotate the motorized turntable, thereby rotating the object 18 one or multiple turns during an examination. The linear positioning subsystem 24 may be employed to enable the object 18 to be displaced linearly, such as by moving a table or support on which the object 18 rests. Thus, in one embodiment, the table may be linearly moved within a gantry to generate images of particular areas of the object 18.

Additionally, the radiation source 12 may be controlled by a radiation controller 30 provided as part of the system controller 22. Particularly, the radiation controller 30 may be configured to provide power and timing signals to the radiation source 12. Further, the system controller 22 may include data acquisition circuitry 32. In this exemplary embodiment, the detector array 16 is coupled to the system controller 22, and more particularly to the data acquisition circuitry 32. The data acquisition circuitry 32 receives data collected by readout electronics of the detector array 16. The data acquisition circuitry 32 typically receives sampled analog signals from the detector array 16 and converts the data to digital signals for subsequent processing and reconstruction by an image reconstructor 34 and/or a computer 36.

Moreover, the computer 36 is typically operationally coupled to the system controller 22. The image reconstructor 34 may be coupled to or may be a part of the computer 36. Also, the sampled and digitized data collected by the data acquisition circuitry 32 may be transmitted to the image reconstructor 34 and/or the computer 36 for subsequent processing and reconstruction. For example, the data collected from the detector array 16 may undergo pre-processing and calibration at the data acquisition circuitry 32, the image reconstructor 34, and/or the computer 36 to condition the data to represent the line integrals of the attenuation coefficients of the scanned objects. The processed data, commonly called projections, may then be reordered, filtered, and back-projected to formulate an image of the scanned area, as will be discussed in greater detail hereinafter. Although the present technique may be used with projection X-ray systems, when used with CT or tomosynthesis systems, in addition to typical filtered back-projection reconstruction algorithms, any suitable reconstruction algorithm may be employed, including statistical reconstruction approaches. Once reconstructed, the image produced by the imaging system 10 may reveal internal as well as external features of the object 18 which may be used for diagnosis, evaluation, and so forth.

Furthermore, the computer 36 may include or be in communication with a memory 38 that may be configured to store data processed by the computer 36 or data to be processed by the computer 36. It should be understood that any type of computer accessible memory device capable of storing the desired amount of data and/or code may be utilized by such an exemplary imaging system 10. Moreover, the memory 38 may comprise one or more memory devices, such as magnetic, solid state, or optical devices, of similar or different types, which may be local and/or remote to the system 10. The memory 38 may store data, processing parameters, and/or computer programs comprising one or more routines for performing the processes described herein. Furthermore, memory 38 may be operationally associated with the system controller 22 to facilitate the storage of acquired data.

In addition, the computer 36 may also be adapted to control features enabled by the system controller 22, such as scanning operations and/or data acquisition. Furthermore, the computer 36 may be configured to receive commands and scanning parameters from an operator via an operator workstation 40. For example, the operator workstation 40 may be equipped with a keyboard and/or other input devices by which an operator may control the imaging system 10. Thus, the operator may observe the reconstructed image and other data relevant to the system from computer 36, initiate imaging, select a spectrum for imaging and so forth.

Also as illustrated in FIG. 1, a display 42 may be operationally coupled to the operator workstation 40 and/or the computer 36 and may be utilized to observe the reconstructed image and/or to control imaging. Additionally, the scanned image may also be printed by a printer 44 which may be coupled to the computer 36 and/or the operator workstation 40, either directly or over a network. Further, the operator workstation 40 and/or the computer 36 may be coupled to a picture archiving and communications system (PACS). In such an embodiment, the PACS might be coupled to a remote system, such as a radiology department information system (RIS), hospital information system (HIS) or to an internal or external network, so that others at different locations may gain access to the image data. It should be further noted that the computer 36 and/or operator workstation 40 may be coupled to other output devices that may include standard or special purpose computer monitors and associated processing circuitry. Furthermore, additional operator workstations may be further linked in the imaging system 10 for outputting system parameters, requesting inspection, viewing images, and so forth, so that more than one operator may perform operations related to the imaging system 10. For example, one operator may utilize one operator workstation to image acquisition while a second operator utilizes a second operator workstation to reconstruct and/or review the results of the imaging routines. In general, displays, printers, workstations, and similar devices supplied within the imaging system 10 may be local to the data acquisition components, or may be remote from these components linked to the imaging system 10 via one or more configurable networks, such as the Internet, virtual private networks, and so forth.

Figure 2:
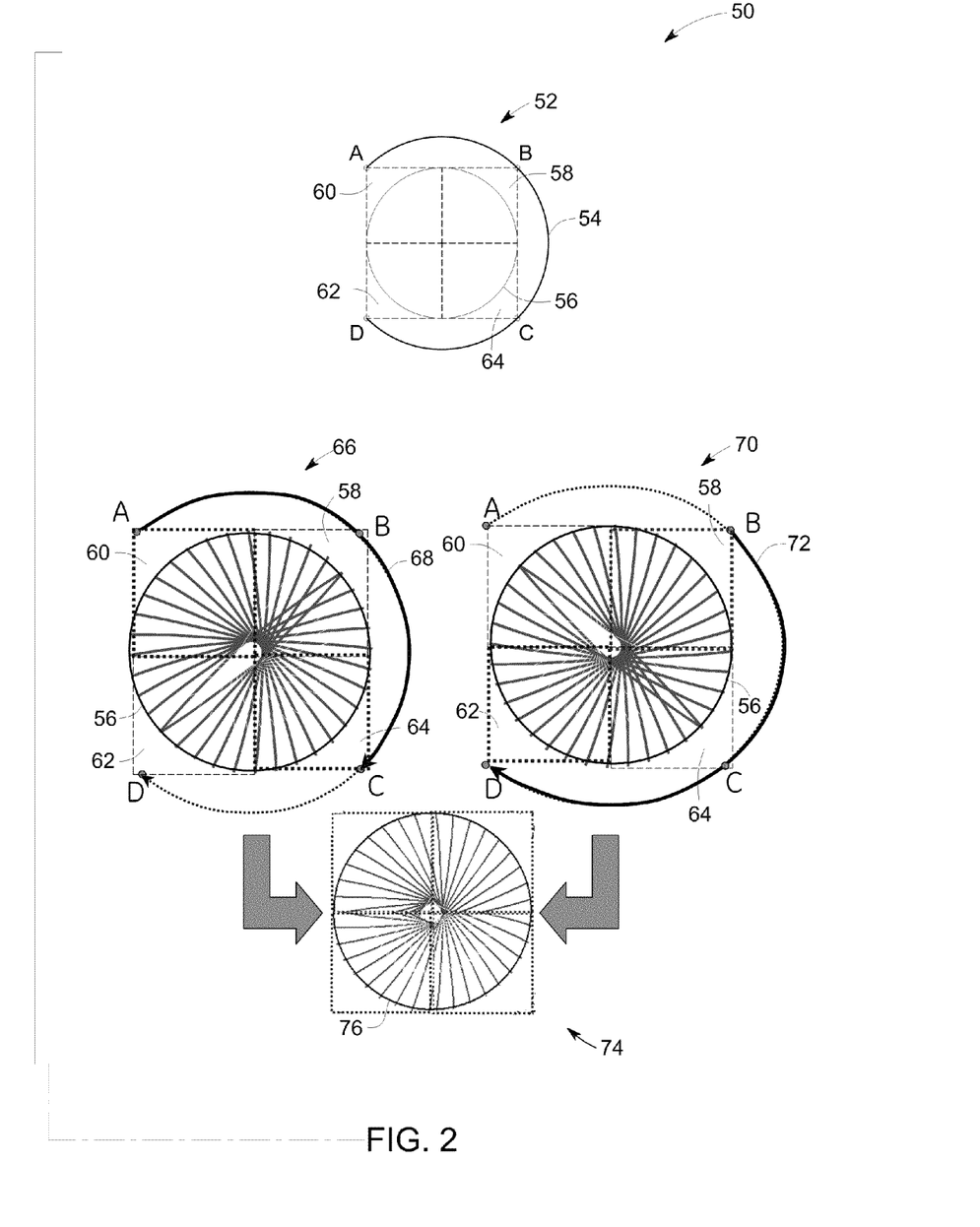
FIG. 2 is a schematic diagram representing an exemplary image reconstruction method according to aspects of the present technique.

Referring now to FIG. 2 a diagrammatic illustration 50 of an exemplary method of image reconstruction according to the aspects of the present technique is illustrated. More particularly, the method for image reconstruction includes performing a short scan for acquiring cone-beam data. The short scan may be less than a full axial scan. In other words, the short scan may include a scan of less than 360 degrees to acquire image data according to aspects of the present technique. Accordingly, the method starts at step 52 where a short scan may be performed to acquire image data. Reference numeral 54 may be representative of a short scan path, and A, B, C, D may be indicative of positions on the short scan path.

According to aspects of the present technique an X-ray source, such as X-ray source 12 of FIG. 1, may be configured to move along the path A, B, C, D to acquire data corresponding to the short scan. Further, reference numeral 56 may be representative of a Radon sphere for an image location in the z-axis but not in the x-y plane.

Subsequently, in accordance with exemplary aspects of the present technique, at step 66 a first image reconstruction may be performed using the acquired scan data corresponding to positions A through C represented by path A-B-C 68 to obtain a first image volume. It may be noted that positions B and C may be dependent on the image location that is being reconstructed. Moreover, according to the aspects of the present technique, a weighting function may be employed while generating the first image volume. The view weighting that is employed may be normalized such that the sum of the weights applied for the conjugate rays is 1. As will be appreciated, for a short scan data acquisition there may be a non-uniform data redundancy since some planes may intersect the source trajectory once while the other planes may intersect the source trajectory twice. It may also be noted that certain planes may not intersect the source trajectory at all. Therefore, according to exemplary aspects of the present technique, the data corresponding to the regions where some planes intersect the source trajectory greater than or less than once may be filtered out. By way of example, for the first image reconstruction of step 66, it may be noted that some planes in the first quadrant 58 intersect the trajectory twice, while some planes in the third quadrant 62 do not intersect the source trajectory at all. Hence for the first image reconstruction data from the first quadrant 58 and the third quadrant 62 may be filtered out. In one embodiment, a filter may be applied to filter the redundant short scan data associated with the path A-B-C 68.

Similarly, as indicated by step 70 a second image reconstruction may be performed by employing acquired data corresponding to positions B through position D represented by path B-C-D 72 to obtain a second image volume. According to an exemplary embodiment, for the second image reconstruction of step 70 the data corresponding to the second quadrant 60 and the fourth quadrant 64 may be filtered out. In one embodiment, a filter may be applied to filter the redundant short scan data associated with the path B-C-D 68. Thereafter, the first and second image volumes may be combined to produce a final image volume 74.

In one embodiment, more than two image reconstructions may be performed as described above to obtain more than two image volumes. Further, filters may be applied to at least two image volumes. According to aspects of the present technique, the filters may include binary functions in a Fourier domain. These image volumes may then be combined to produce a final image volume 76.

In accordance with the aspects of the present techniques various filters, such as Fourier domain weighting functions may be used to combine the multiple image volumes. Often, two reconstructions may be performed for example A to C based and B to D based, as described earlier. As illustrated in FIG. 2 the Fourier space may be divided into four quadrants based on the angle of the short scan centerview (see FIG. 2). In one embodiment, a "sharp" or binary weighting function wherein two diagonal quadrants for example the first quadrant 58 and the third quadrant 62 receive a weight of 1 for the first reconstruction, while the second quadrant 60 and the fourth quadrant 64 receive a weight of 0. Similarly, for the second reconstruction, the weighting function may be the complement of the first reconstruction. More particularly, the second quadrant 60 and the fourth quadrant 64 receive a weight of 1 and the first quadrant 58 and the third quadrant 62 receive a weight of 0. These filters remove most of the frequencies that may be either redundantly measured or may not have been measured at all in the view-weighted data. Additionally, the filters tend to preserve data that may be acquired when the source is nearest the short scan centerview that may provide a good temporal resolution when imaging dynamic objects.

Further, in one embodiment, it may be useful to smooth the weighting functions near the quadrant boundaries so as to reduce the streakiness of motion artifacts or truncation artifacts for slices that may be far from the mid-plane. The weight may be defined as follows in polar coordinates:

$$w\_1(r,\theta)=\max(0,\min(1,\cos(\theta)\hat{0}2-0.5)/W+0.5)) \quad (1)$$

$$w\_2(r,\theta)=\max(0,\min(1,\sin(\theta)\hat{0}2-0.5)/W+0.5)) \quad (2)$$

where w_1 is the first view weighting function and w_2 is the second view weighting function In the present embodiment, the weight may be substantially equal to 1 for most of the two quadrants that we want to preserve and 0 for most of the two quadrants with corrupted data, but there are transition regions near the quadrant boundaries. The parameter W is a constant. In one example, W may be 0.3. Moreover, the parameter W determines the width of the transition region. It may be noted that as in the binary weighting case, these filters are complementary to each other.

In accordance with aspects of present techniques, image reconstruction of three volumes may be performed: the first image reconstruction based on data from A to B, the second image reconstruction based on the data from B to C, and the third image reconstruction based on the data from C to D to obtain three image volumes. In the present embodiment, the second volume may be passed through without filtering due to the linearity of the Fourier transform, while the complementary filters as described above may be applied to the first and third volumes.

Further, examples of weighting function such as normal weighting function and a smooth weighting function that may be applied on the scan data corresponding to path A-B-C 68 will be described in greater detail with respect to FIG. 3 and FIG. 6. Similarly a smooth weighting function that may be applied on the scan data corresponding to path B-C-D 72 will be described in greater detail with respect to FIG. 7.

Figure 3:
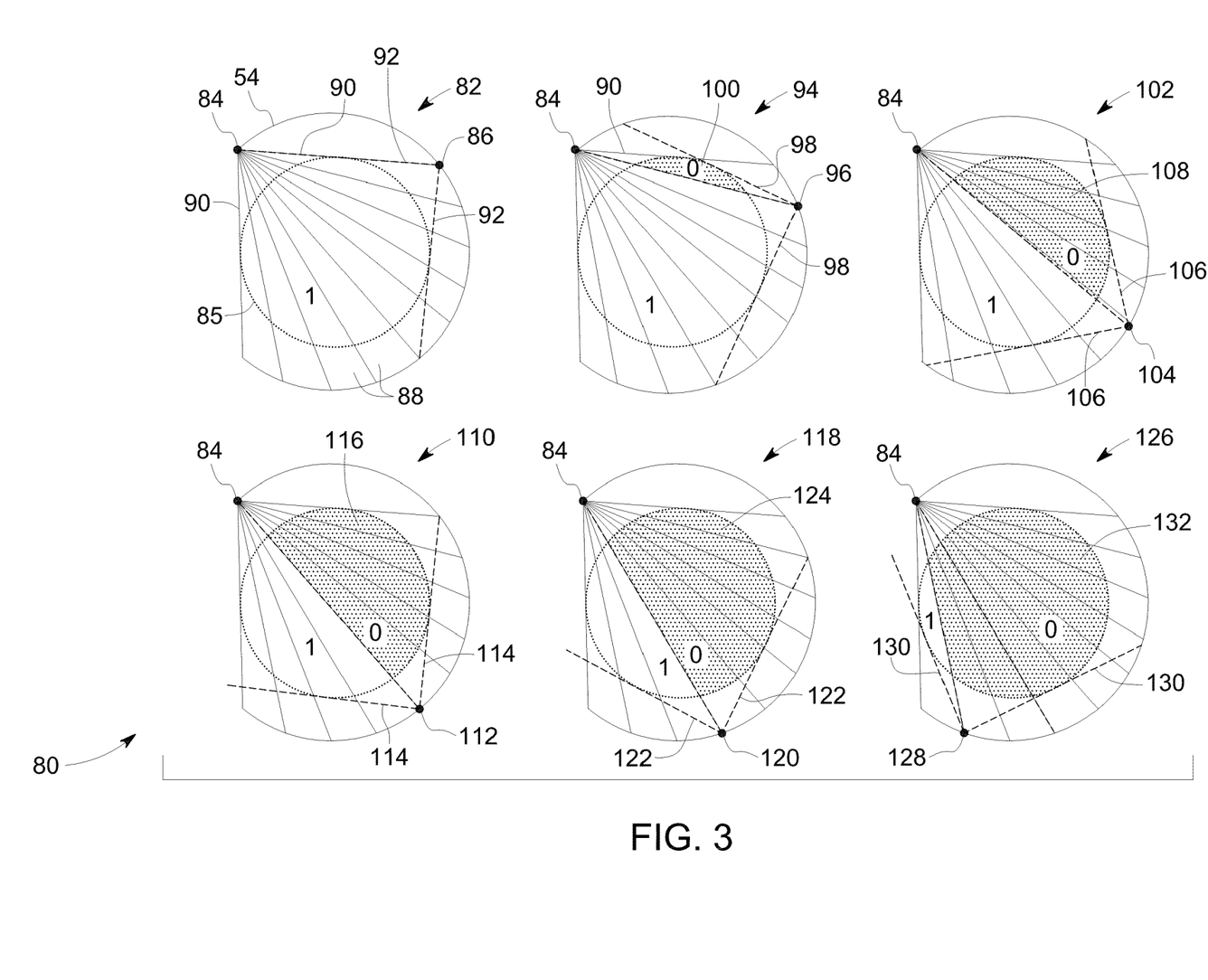
FIG. 3 is a diagram illustrating view weighting according to aspects of the present technique.

Referring now to FIG. 3, a diagrammatical representation 80 of an exemplary view weighting method according to aspects of the present technique is shown. More particularly, the diagrammatical representation 80 illustrates application of a weighting function to the data used to produce the first image reconstruction 66 of FIG. 2. A panel 82 representing rotation of X-ray source 12 of FIG. 1 along the short scan path 54 between a starting position 84 of the X-ray source 12 and a second position 86 of the X-ray source 12 is illustrated. The X-ray source 12 emits X-rays that pass through the field of view 85. The X-rays emitted from the starting position 84 may be representative of the critical rays 88 having a span 90. Here, span of x-rays is the angular measure of X-rays emanating from the X-ray source 12. Critical rays may be representative of rays through point A for first image recon and point D for the second image recon. Span may be representative of fan beam coverage of an X-ray beam. In other words, the span is representative of a full fan of X-rays at a given source position. Similarly, rays emitted from the second source position 86 may have a span 92. In accordance with aspects of the present technique a datum may be retained and/or discarded by applying a view weighting function, such as a binary view weighting function. By way of example, data corresponding to certain regions may be retained by applying a view weighting function equal to 1, while data corresponding to certain other regions may be discarded by weighting that data with a view weighting function equal to 0. It may be noted that the weighting functions generally provide weights that sum to one for conjugate rays.

Accordingly, a view-weighting function equal to 1 may be applied to the projection data from any source position that lies between the starting position 84 and the second position 86 of the X-ray source 12. In other words, all of the data corresponding to a region associated with the second position 86 of the source may be retained by weighting that data with a view weighting function equal to 1.

The panel 94 may be representative of the rotation of the X-ray source to a third position 96 with a span 98 of the emitted X-rays. As illustrated in panel 94, the X-rays emitted by the X-ray source 12 in the first position 84 and the third position 96 intersect in a first region 100. In accordance with one embodiment, a weighting function that has a value substantially equal to zero may be applied on the first region 100, the reason these rays are weighted by zero is because their conjugate rays were weighted by 1, while the data in remaining region in the field of view 85 may be weighted with value that is substantially equal to 1. Similarly, panels 102, 110, 118 and 126 respectively illustrate a fourth position 104, a fifth position 112, a sixth position 120 and a seventh position 128 of the X-ray source with corresponding overlap region 106, 116, 124 and 132 indicated by shading. In accordance with one embodiment, the acquired data in these overlap regions have a weighting function with a value substantially equal to zero. Further, the technique described above for the first image reconstruction with regard to path A-B-C may also be applied to the second image reconstruction for path B-C-D.

Figure 4:
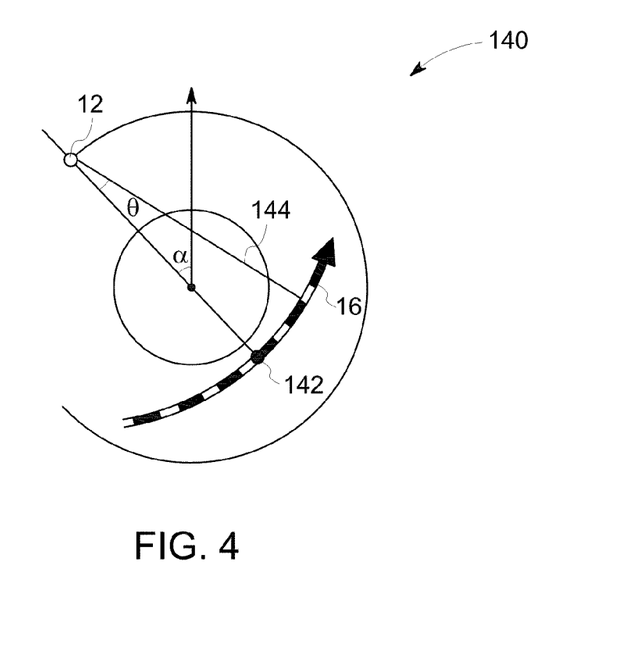
FIG. 4 is a diagram illustrating a view angle and a fan angle.

As will be appreciated, an X-ray source 12 emits a beam of X-rays, which has a view angle and a fan angle. FIG. 4 is a diagrammatic representation 140 of a fan angle and a view angle. More particularly, an X-ray 144 is illustrated with a fan angle θ. The X-ray 144 is illustrated originating from the source 12 striking a channel of detectors such as detector 16 of FIG. 1. The divergence of the X-ray 144 from the center 142 of the detector array is the fan angle represented by θ. A view angle α is also illustrated where a view angle is the angle of the source focal spot with respect to the starting point of X-ray source 12.

Figure 5:
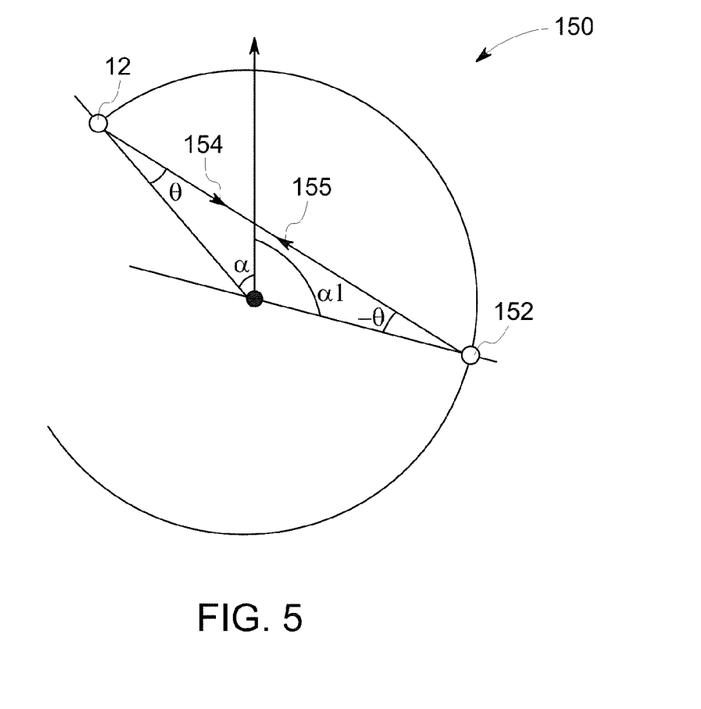
FIG. 5 illustrates a view angle and a fan angle for an X-ray source and a conjugate X-ray source according to an aspect of the present technique.

FIG. 5 is a diagrammatic representation 150 of a fan angle and a view angle for the X-ray source 12 and a conjugate X-ray source 152. As described earlier, the source 12 moves during scan in a clockwise direction. The conjugate X-ray source 152 is representative of the location of the source, which emits X-rays that travel in opposite direction to the rays emitted by source 12. As illustrated, the X-ray source 12 emitting an X-ray 154 has a fan angle and view angle θ and α respectively. The conjugate X-ray source 152 also emits an X-ray 155 that has a fan angle and a view angle −θ and α1 respectively, where α1=180+α+2θ. As a convention, all the angles may be measured in a clockwise direction. As described earlier, the image reconstructions using data acquired during the short scan may result in a corresponding plurality of co-located image volumes. These plurality of co-located image volumes may be obtained by using different view weighting functions. According to aspects of present technique, the view weighting functions satisfy the following normalization condition:

$$w(\text{view, fan})+w(\text{view}+180+2*\text{fan},-\text{fan})=1 \quad (3)$$

where, w is the weighting function, view is the view angle, and fan is the fan angle It may be further noted that the view weighting depends on both the view angle and the fan angle.

In one embodiment, the plurality of image volumes that may be reconstructed may include two image volumes. For reconstructing two image volumes, two view weighting functions may be applied which depend on both the view angle and the fan angle. Further, the two view weighting functions may be symmetric relative to one another such that:

$$w\_1(\text{center\_view}+\text{view}, \text{fan}) = w\_2(\text{center\_view}-\text{view}, -\text{fan}) \quad (4)$$

where, $w\_1$ is a first view weighting function and $w\_2$ is a second view weighting function.

Figure 6:
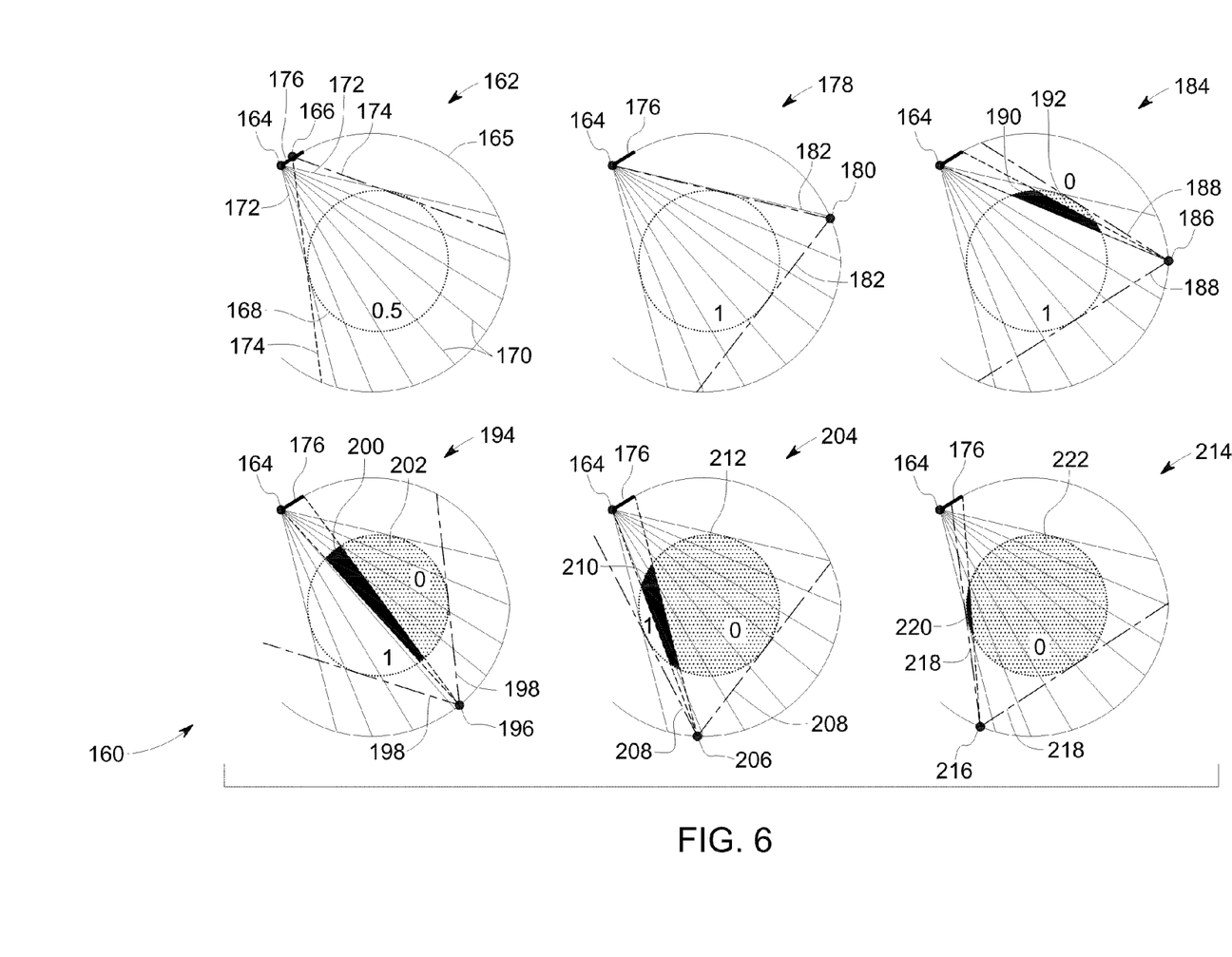
FIG. 6 illustrates smooth view weighting functions applied to a first image reconstruction of an image volume according to aspects of the present technique.

Turning now to FIG. 6 another aspect of the present technique for applying a smooth weighting function is illustrated. More particularly, a diagrammatic representation 160 of application of a smooth weighting function for use with the first image reconstruction 66 of FIG. 2 is illustrated. In accordance with aspects of the present technique, a smooth weighting function means that a fractional weight may be applied to the projection data in a transition region as will be described later. A panel 162 representing rotation of an X-ray source such as the X-ray source 12 of FIG. 1 along a transition path 176 is illustrated. The source 12 emits X-rays that pass through a field of view 168 corresponding to the source 12. The X-rays emitted from the X-ray source at the starting position 164 are the critical rays 170 having a span 172. Similarly, rays emitted from the second source position 166 may have a span 174. The second source position 166 lies in a transition path 176. In the illustrated embodiment the second source position 166 may be located at a position in the transition path 176, which may be for example, about 10 degrees angular distance (as shown by "delta" in FIG. 8) from the starting position 164 of the X-ray source 12 in one embodiment. In accordance with aspects of the present technique, when the source position is in the transition path 176, a weighting function that changes from 0 to 1.0 in the transition path may be applied to the projection data. More particularly, the weighting function in the present embodiment is 0 for rays emanating from starting position 164, the weighting function 0.5 for rays emanating from second source location 166, and a weighting function of 1 for rays emanating from other end of the transition path 176. It may be noted that the weighting function may vary smoothly as the source travels along the transition path 176.

The panel 178 represents the rotation of the X-ray source 12 to a third position 180. The X-ray emitted by the X-ray source 12 at the third position 180 may have a span 182 of the emitted X-rays. It may be noted that the third position 180 of the X-ray source 12 lies outside the transition path 176. Accordingly, in one embodiment a weighting function with value substantially equal to 1 may be applied to the transform of the image data. As the X-ray source 12 rotates further to a fourth position 186 illustrated by panel 184, view weightings may be applied to transform of the image data based on the location of the data. More particularly, a weighting of value substantially equal to zero may be applied on region 192, weighting between 0 and 1 may be applied on the transition region 190 and the remaining region in the field of view 168 may be weighted with value substantially equal to 1. Similarly, panel 194, 204, 214 illustrate a fifth position 196, a sixth position 206, and a seventh position 216 of the X-ray source with the overlap region of the acquired data 202, 212 and 222 may have a weighting substantially equal to zero and the transition region 200, 210 and 220 with weighting between 0 and 1 may be applied respectively. Further, the remaining region in each panel may be weighted with value substantially equal to 1.

Figure 7:
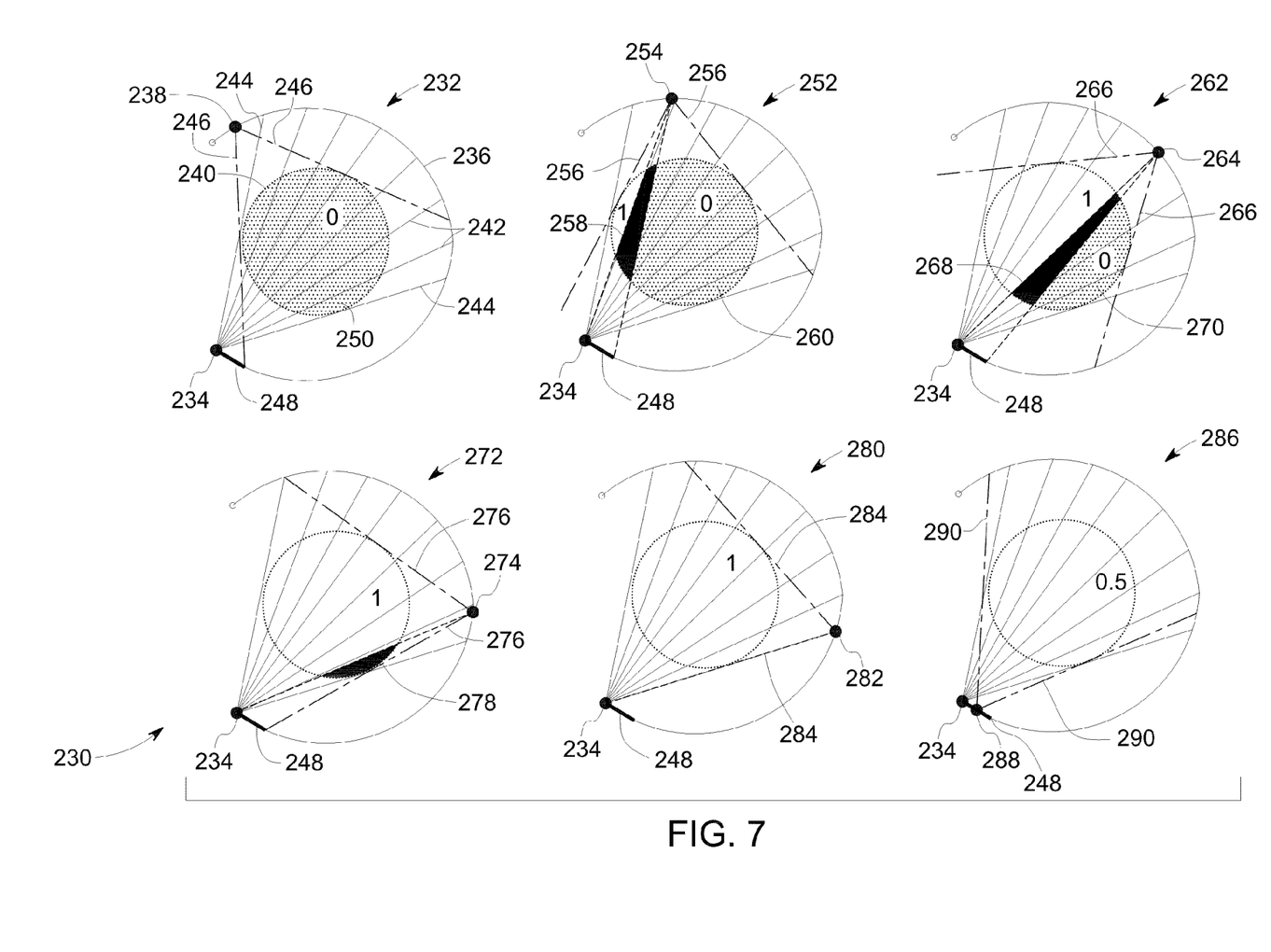
FIG. 7 illustrates a smooth view weighting functions applied to a first image reconstruction of an image volume according to an aspect of the present technique.

Referring now to FIG. 7, a diagrammatic illustration 230 of applying a smooth weighting reconstruction for a second image reconstruction such as 70 (path B-C-D 72) of FIG. 2 is illustrated. Moreover, a transition path 248 on path B-C-D 72 is illustrated, which in one example, may be about 10 degrees angular distance from the final position 234 of the X-ray source 12. In accordance with aspects of the present technique, when the source position is in the transition path 248, a weighting function that has a value that changes smoothly from 0 to 1.0 may be applied to the projection data. A panel 232 representing rotation of X-ray source 12 of FIG. 1 along a short scan path 236 between a first position 238 and a final position 234 is shown. The source 12 emits X-rays that pass through a field of view 240 corresponding to the source 12. The X-rays emitted from the final position 234 are the critical rays 242 having a span 244. Similarly rays emitted from the first source position 238 may have a span 246. In accordance with aspects of the present technique, a weighting substantially equal to zero may be applied to the projection data in a first overlap region 250 of the X-rays emitted by the X-ray source 12.

Further, a panel 252 representing a second position 254 with a span 256 of the emitted X-rays illustrates a weight that may be applied on the projection data. More particularly, a weighting function with a value substantially equal to zero may be applied to the projection data corresponding to overlap region 260, while a weighting function with value that changes smoothly from 0 to 1.0 may be applied to image data corresponding to the transition region 258 and the remaining region in the field of view 240 may be weighted with value substantially equal to 1.

Similarly, panel 262 illustrates a third position 264 with a span 266, of the X-ray source with the overlap region 270 of the acquired data where a weighting function with value substantially equal to zero and the transition region 268 with weighting function with value that changes smoothly from 0 to 1.0 may be applied respectively.

Panel 272 illustrates a fourth position 274 of the X-ray source 12 having a span 276 of emitted X-rays, a weighting value that changes smoothly from 0 to 1.0 may be applied to the projection data corresponding to transition region 278 and the projection data in remaining region in the field of view may be weighted with value substantially equal to 1. Furthermore, panel 280 illustrates a fifth position 282 of the X-ray source 12. Here, the span 284 of X-rays emitted from the X-ray source does not overlap with the critical rays 242 of the final source position 234 within the field of view 240. Hence, a weighting function substantially equal to 1 may be applied to the transform of the image data. Finally, a panel 286 illustrates rotation of X-ray source 12 in a transition path 248, which includes a sixth position 288. It may be noted that at the sixth position 288 the X-ray source 12 may have a span 290 of the emitted rays. Also, the sixth position 288 of the X-ray source 12 is in the transition path 248; accordingly a weighting function between zero and one may be applied to the projection data. In one example, for the sixth position 288 a weight with value equal to 0.5 may be applied to the projection data in the field of view as illustrated.

Figure 8:
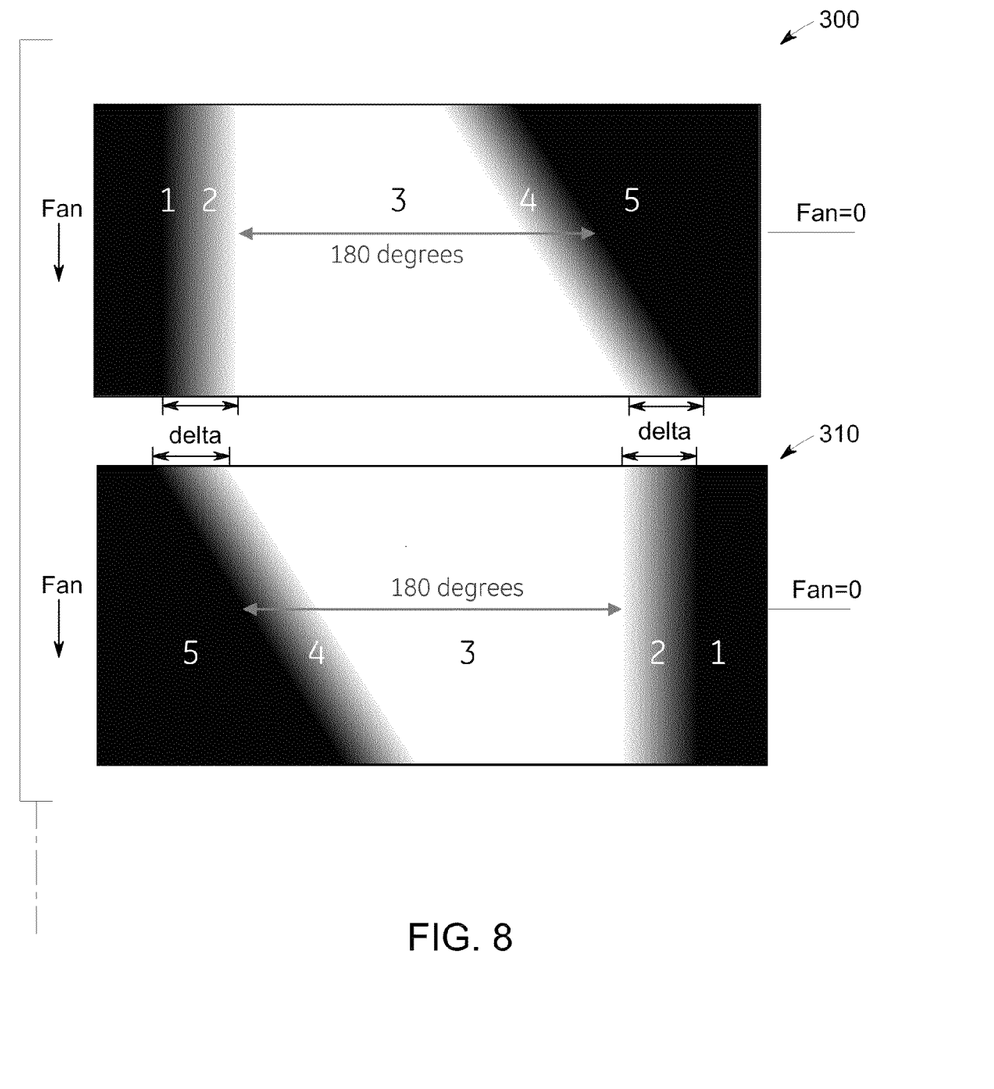
FIG. 8 is a pictorial representation of view weighting functions applied to two different reconstruction of the image volume according to aspects of the present technique.

FIG. 8 is a representation of the weighting functions that may be applied on various regions. The horizontal axis represents a view angle and the vertical axis represents a fan angle. The intensity at each pixel represents the value of the weighting function at that particular (view, fan) pair. As illustrated, the various weighting functions are applied along the scan path A-B-C 68 is diagrammatically represented by reference numeral 300 and the weighting functions applied along the path B-C-D 72 is represented by reference numeral 310. The various regions are represented by numerals 1, 2, 3, 4 and 5. For the starting point, indicated by position A, the weighting function on region 1 has a value equal to zero. When the source moves by a small angle delta which is in the region between the starting position A and a small angle delta, the weighting function that may be applied depends on the following equation:

For region 2, $$w(\text{view, fan}) = f(\text{view} - (\text{view\_1})). \quad (5)$$

The weighting function is $$w(\text{view, fan}) = 1 \quad (6)$$

For region 3, when view is between (view_1+delta) and (view_1+180°+2*fan)
The weighting function is $$w(\text{view, fan}) = f(\text{view} - 1 + 180° + 2*\text{fan} + \text{delta} - \text{view}) \quad (7)$$

For region 4 where the source location is between (view_1+180°+2*fan) and (view_1+180°+2*fan+delta).
The weighting function is $$w(\text{view, fan}) = 0 \quad (8)$$

For region 5, where view is greater than (view_1+180°+2*fan+delta) and for region 1, where view is less than view_1.

As hereinabove, view_1 is the starting point of the source location and may also be written as:

$$\text{view\_1} = \frac{\text{center\_view} - \text{shortscan\_length}}{2} \quad (9)$$

where center_view is the central view of data used for reconstruction, shortscan_length is the difference between the first and last view angle of the data used for reconstruction.
Therefore, center_view is the starting point plus half of the short scan length. f(view) is a smooth function with f(0)=0 and f(delta)=1 for some small angle delta which corresponds to the length of the transition path.

Figure 9:
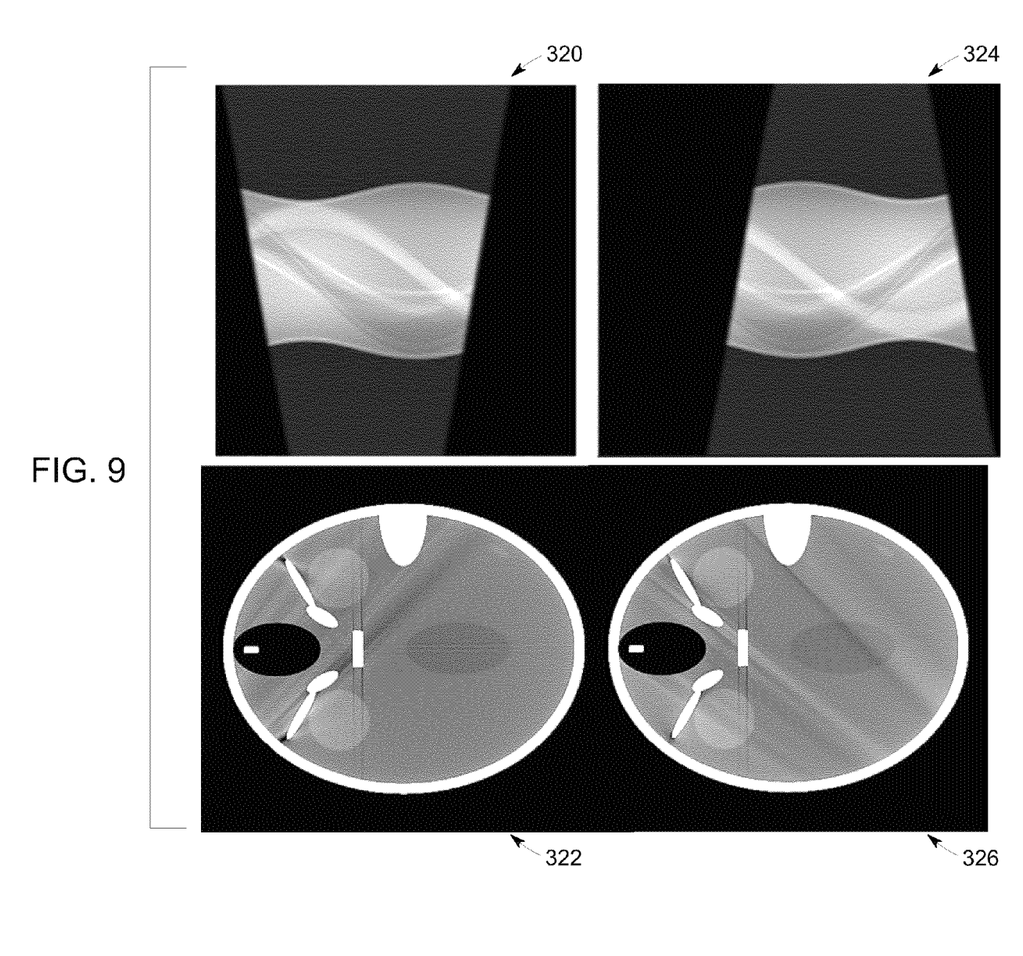
FIG. 9 is a pictorial representation of projection data before backprojection and images obtained after backprojection on the data in accordance with aspects of the present technique.

FIG. 9 illustrates sinograms 320 and 324 obtained after weighting has been applied as described in FIG. 8 and a rebinning to a cone parallel geometry has also been performed for a single detector row. The full sinograms may then be reconstructed to obtain the image volumes. A single (off-center) slice of these image volumes is shown in 322 and 326 respectively.

Figure 10:
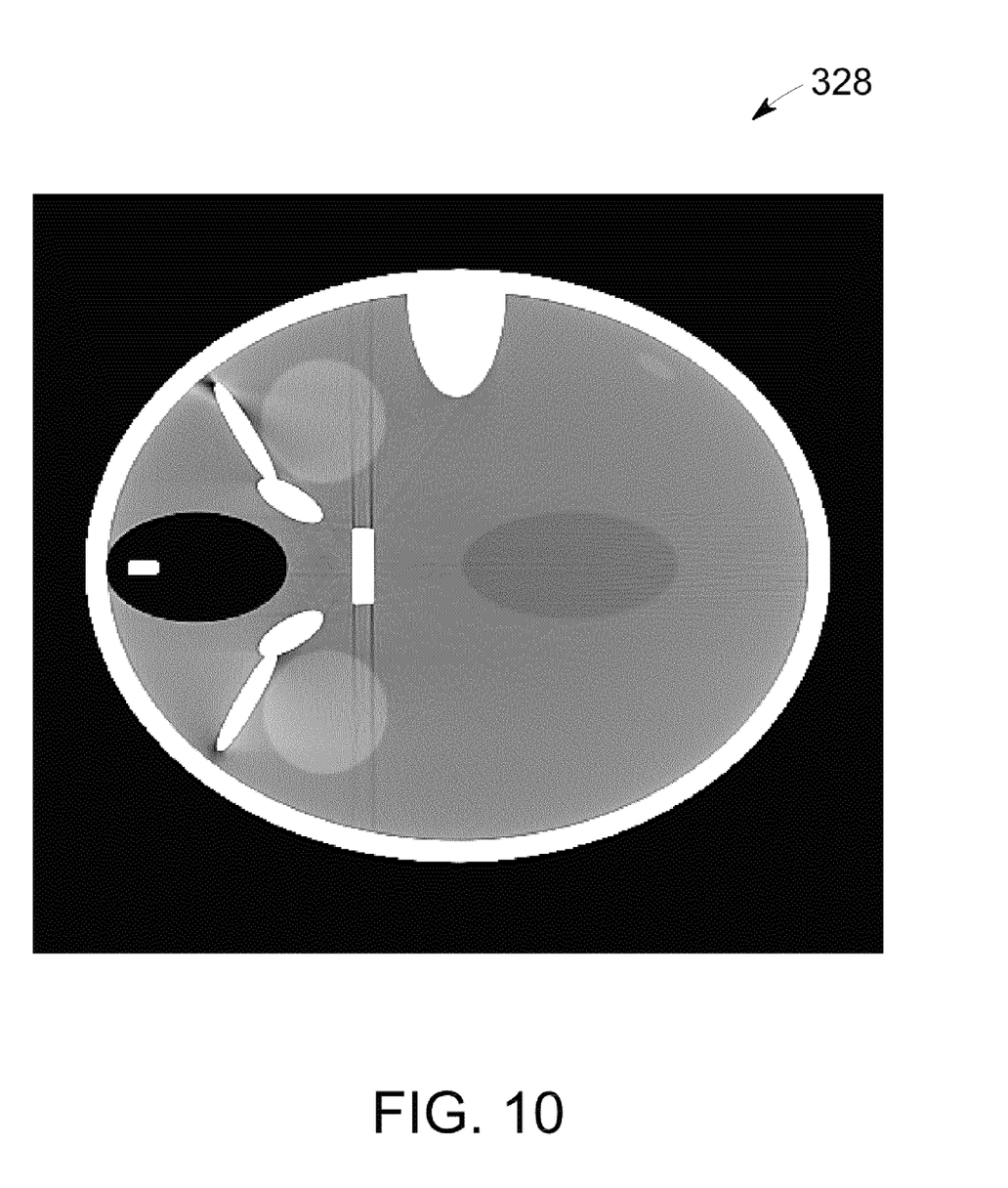
FIG. 10 is a pictorial representation of an image generated by combining the images of FIG. 9 according to an aspect of the present technique.

Turning now to FIG. 10 a resultant image 328 that is obtained after combining the two images 322 and 326 of FIG. 9 by the technique described in FIG. 2 is illustrated. In one embodiment, a Fourier transform, weighting, summation, and inverse Fourier transform may be applied on the on the images 322 and 326 to obtain the final image 328.

Figure 11:
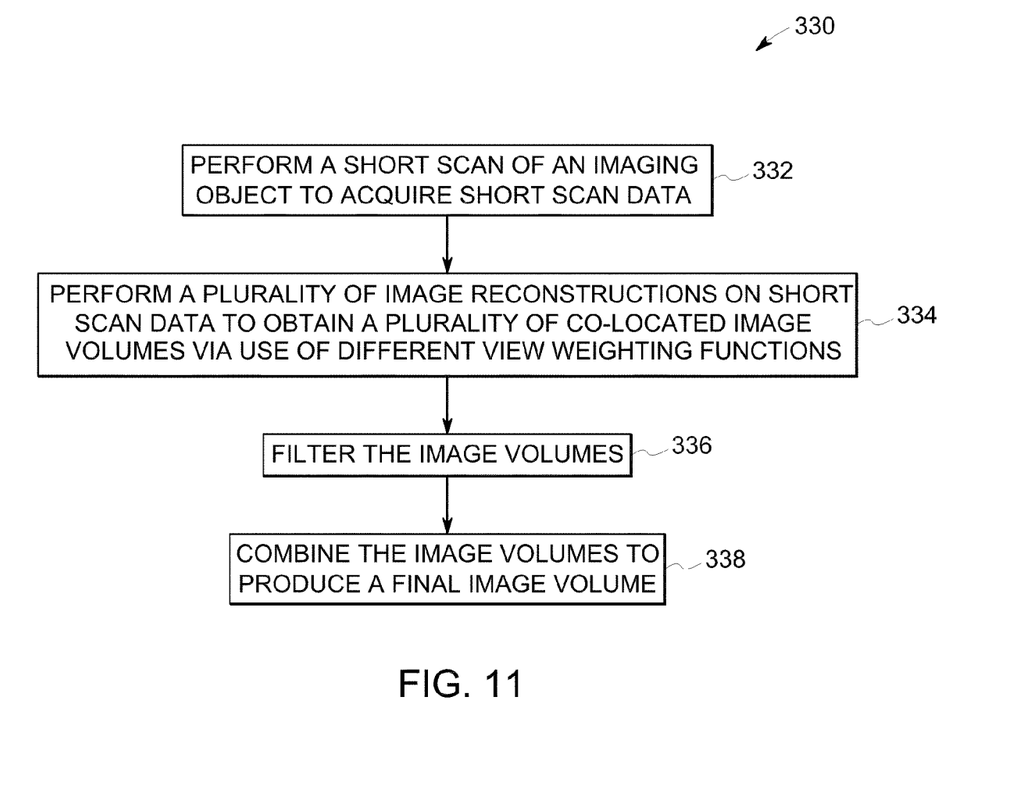
FIG. 11 is flow chart depicting a method for reconstructing an image according to aspects of the present technique.

FIG. 11 is a flowchart 330 illustrating an exemplary method of image reconstruction according to aspects of the present technique. The method starts at step 332 where a short scan of an imaging object may be performed to acquire a short scan data, subsequently a plurality of image reconstructions may be performed using the short scan data to obtain a plurality of co-located image volumes via use of different view weighting functions as indicated by step 334. Moreover at step 336, image volumes may be filtered. Also, the image volumes may be combined to obtain a final image volume depicted by step 338.

Furthermore, according to another aspect of the present technique the method of image reconstruction may be performed using a parallel derivative, thereafter a Hilbert transform may be applied in the cone-beam geometry, and a cone-beam backprojection. In this embodiment, a reciprocal-distance weight must be applied on the backprojection. Further, filtering may be carried out in planes tangent to the vertex path. The view weighting function may be applied after filtering.

In accordance with yet another aspect of the present technique, the exemplary image reconstruction also referred to as the butterfly image reconstruction may be performed using a ramp filter on the data in the cone-beam geometry and back-projecting the data in cone-beam geometry. In this embodiment, a reciprocal-distance-squared weight may be applied and a boundary term based on the Hilbert transform may be included wherever the view-weighting derivative is non-zero. The filtering may be carried out in planes tangent to the vertex path. Further, view weighting may be applied after filtering.

Moreover, according to another aspect of the present technique, the image reconstruction may be performed using a parallel derivative, a Hilbert transform in the cone-beam geometry, followed by rebinning the data to cone-parallel geometry, and backprojecting the data in a cone-parallel-geometry. In this embodiment, distance based weighting may not be applied, only view based weighting may be applied. Further, view weighting may be applied after filtering.

Additionally, according to yet another aspect of the present technique, reconstruction of plurality of image volumes is performed by rebinning the data to cone-parallel geometry, a ramp filter may then be applied along the rebinned detector rows to filter the data, thereafter view weighting may be applied, and finally the image volumes may be backprojected in the cone-parallel-geometry. In this embodiment, no distance based weighting may be applied in the image reconstruction process.

Further, according to another aspect of the present technique, reconstruction of plurality of image volumes may be performed by applying the view weighting and rebinning to cone-parallel geometry first. It may be noted that the view weighting and rebinning to cone-parallel geometry may be applied in either order. Thereafter, a ramp filter may be applied and finally a cone-parallel-geometry backprojection may be performed on the projection data to produce an image volume. Further, in the present embodiment a smooth view weighting is applied. Moreover, distance based weighting is not applied in the present embodiment.

As will be appreciated by those of ordinary skill in the art, the foregoing example, demonstrations, and process steps may be implemented by suitable code on a processor-based system, such as a general-purpose or special-purpose computer. It should also be noted that different implementations of the present technique may perform some or all of the steps described herein in different orders or substantially concurrently, that is, in parallel. Furthermore, the functions may be implemented in a variety of programming languages, including but not limited to C++ or Java. Such code, as will be appreciated by those of ordinary skill in the art, may be stored or adapted for storage on one or more tangible, machine readable media, such as on memory chips, local or remote hard disks, optical disks (that is, CDs or DVDs), or other media, which may be accessed by a processor-based system to execute the stored code. Note that the tangible media may comprise paper or another suitable medium upon which the instructions are printed. For instance, the instructions can be electronically captured via optical scanning of the paper or other medium, then compiled, interpreted or otherwise processed in a suitable manner if necessary, and then stored in a computer memory.

The exemplary image reconstruction technique as discussed hereinabove has several advantages, including improved image quality. The technique reduces cone-beam artifacts, which may help in increasing the ability of radiologists to be able to make better decisions based on the images.

The above-description of the embodiments of the method for reconstructing an image and the system for reconstructing an image have the technical effect of improving workflow by enhancing image quality and reducing image artifacts, thereby allowing acceleration of image processing applications.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of performing computed tomography image reconstruction comprising:
  performing a short scan of an imaging object to acquire a short scan data;
  performing a plurality of image reconstructions based on the short scan data wherein the plurality of image reconstructions result in a corresponding plurality of image volumes wherein the plurality of image reconstructions use different view weighting functions;
  filtering the plurality of image volumes such that when the plurality of image volumes are added together, the frequency domain data is substantially uniformly weighted; and
  combining the plurality of image volumes together to produce a final image volume.

2. The method of claim 1, wherein the short scan is less than 360 degrees.

3. The method of claim 1, wherein the short scan is a sum of 180 degrees and a fan angle.

4. The method of claim 1, wherein performing a plurality of image reconstructions comprises:
  reconstructing two image volumes;
  applying view weighting functions for the two image volumes such that the weighting functions satisfy a following normalization condition, wherein $w(\text{view,fan}) + w(\text{view}+180+2*\text{fan},-\text{fan}) = 1$; and applying filters to the two image volumes which sum to one in the Fourier domain.

5. The method of claim 4, wherein the filters comprise binary functions in the Fourier domain.

6. The method of claim 4, wherein the filters are two-dimensional filters complementary to each other and one of the complementary filters has a value that is higher than the other complementary filter for polar frequencies in two opposing 90 degree sectors of Fourier space, while the value of the other complementary filter is higher in the remaining two 90 degree sectors.

7. The method of claim 6, wherein the complementary filters are binary except within a transition regions.

8. The method of claim 4, wherein:
  the two view weighting function depend only on view angle and fan angle; and
  the two view weighting functions are symmetric relative to one another such that $w\_1(\text{center\_view}+\text{view, fan}) = w\_2(\text{center\_view}-\text{view},-\text{fan})$ where $w\_1$ is a first view weighting function and $w\_2$ is a second view weighting function.

9. The method of claim 8, wherein one of the view weighting functions is defined such that:
  $w(\text{view,fan})=0$ when view is less than view\_1;
  $w(\text{view,fan})=f(\text{view}-(\text{view}\_1))$, when view is between view\_1 and (view\_1+delta);
  $w(\text{view, fan})=1$ when view is between (view\_1+delta) and (view\_1+180°+2*fan);
  $w(\text{view,fan})=f(\text{view}\_1+180°+2*\text{fan}+\text{delta}-\text{view})$, when view is between (view\_1+180°+2*fan) and (view\_1+180°+2*fan+delta);
  $w(\text{view,fan})=0$ when view is greater than (view\_1+180°+2*fan+delta);

$$\text{view\_1} = \frac{\text{center\_view} - \text{shortscan\_length}}{2}; \text{ and}$$

$f(\text{view})$ is a smooth function with $f(0)=0$ and $f(\text{delta})=1$ for some small angle delta.

10. The method of claim 1, wherein performing a plurality of image reconstructions comprises reconstructing three image volumes, wherein:
  a sum of the weighting functions of a first volume and a second volume satisfies the normalization condition $w(\text{view, fan})+w(\text{view}+180+2*\text{fan},-\text{fan})=1$;
  a sum of the weighting functions of the second volume and the third volume also satisfies the normalization condition $w(\text{view, fan})+w(\text{view}+180+2*\text{fan},-\text{fan})=1$; and
  a sum of the filters applied to the first volume and the third volume is one in the Fourier domain.

11. The method of claim 10, wherein the filters are applied to at least two of the image volumes.

12. The method of claim 10, wherein the filter is not applied to the second image volume.

13. The method of claim 10, wherein the filters comprise binary functions in the Fourier domain.

14. The method of claim 10, wherein the filters are two-dimensional filters complementary to each other and one of the complementary filters has a value that is higher than the other complementary filter for polar frequencies in two opposing 90 degree sectors of Fourier space, while the value of the other complementary filter is higher in the remaining two 90 degree sectors.

15. The method of claim 14, wherein the complementary filters are binary except within a transition regions.

16. The method of claim 1, wherein reconstructing the plurality of image volumes comprises:
  applying a parallel derivative and a Hilbert transform in planes tangent to a vertex path in a cone beam geometry to obtain a filtered short scan data;
  applying a view-weighting to the filtered short scan data to obtain a weighted filtered short scan data; and
  backprojecting the weighted filtered short scan data using reciprocal-distance weight.

17. The method of claim 1, wherein reconstructing the plurality of image volumes comprises:
  applying a ramp filter to the short scan data in a cone-beam geometry in planes tangent to a vertex path;
  applying a view weighting to the short scan data to produce a weighted short scan data;
  adding a boundary term based on the Hilbert transform of the short scan data and a derivative of the view weighting function to the weighted short scan data to obtain a result; and
  backprojecting the result with a reciprocal distance squared weight.

18. The method of claim 1, wherein reconstructing the plurality of image volumes comprises:
   applying a parallel derivative and a Hilbert transform in planes tangent to a vertex path in a cone beam geometry to obtain filtered short scan data;
   rebinning the filtered short scan data to a cone-parallel geometry;
   applying a view weight to the rebinned data; and
   backprojecting the rebinned data.

19. The method of claim 1, wherein reconstructing the plurality of image volumes comprises:
   applying a smooth view weighting to the short scan data to obtain a weighted short scan data;
   rebinning the weighted short scan data to a cone parallel geometry to obtain a weighted cone parallel geometry data;
   filtering the weighted cone parallel geometry data with a ramp filter to obtain a filtered data; and
   backprojecting the filtered data in the cone-parallel geometry.

20. The method of claim 1, wherein reconstructing the plurality of image volumes comprises:
   rebinning the short scan data to cone parallel geometry;
   filtering the rebinned short scan data with a ramp filter to obtain a filtered short scan data;
   applying a view weight to the filtered short scan data to obtain a weighted filtered short scan data; and
   backprojecting the weighted filtered short scan data in the cone-parallel geometry.

21. A tomographic imaging apparatus comprising:
   a computer programmed to:
      perform a short scan of an imaging object to acquire a short scan data;
      perform a plurality of image reconstructions based on the short scan data wherein the plurality of image reconstructions result in a corresponding plurality of image volumes wherein the image reconstructions use different view weighting functions;
      filter the plurality of image volumes such that when the plurality of image volumes are added together, the frequency domain data is substantially uniformly weighted; and
      combining the plurality of image volumes together to produce a final image volume; and
   a display unit for displaying the final image volume.

22. A non-transitory computer readable media embodying instructions, which when executed by a processor cause the computer to perform a method comprising:
   performing a short scan of an imaging object to acquire a short scan data;
   performing a plurality of image reconstructions based on the short scan data wherein the plurality of image reconstructions result in a corresponding plurality of image volumes wherein the image reconstructions use different view weighting function;
   filtering the plurality of image volumes such that when the plurality of image volumes are added together, the frequency domain data is substantially uniformly weighted; and
   combining the plurality of image volumes together to produce a final image volume.

* * * * *